(12) United States Patent
Haanstra et al.

(10) Patent No.: US 6,672,164 B1
(45) Date of Patent: Jan. 6, 2004

(54) PROCESS FOR DETERMINING THE POLYMER CONCENTRATION IN A SPINNING DOPE SOLUTION

(75) Inventors: Willem G. Haanstra, Westervoort (NL); Hendrikus J. M. Busschers, Enschede (NL); Hans Lammers, Arnhem (NL)

(73) Assignee: Teijin Twaron B.V., Arnhem (NL)

( * ) Notice: Subject to any disclaimer, the term of this patent is extended or adjusted under 35 U.S.C. 154(b) by 0 days.

(21) Appl. No.: 10/009,804

(22) PCT Filed: May 23, 2000

(86) PCT No.: PCT/EP00/04729

§ 371 (c)(1),
(2), (4) Date: Dec. 13, 2001

(87) PCT Pub. No.: WO00/77515

PCT Pub. Date: Dec. 21, 2000

Related U.S. Application Data

(60) Provisional application No. 60/145,600, filed on Jul. 26, 1999.

(30) Foreign Application Priority Data

Jun. 16, 1999 (EP) .............................................. 99201907

(51) Int. Cl.⁷ .............................................. G01N 29/04
(52) U.S. Cl. .............................. 73/597; 73/598; 73/602
(58) Field of Search .......................... 73/597, 598, 601, 73/602, 61.49, 64.53; 428/364

(56) References Cited

U.S. PATENT DOCUMENTS

| 5,141,642 | A | * | 8/1992 | Kusuki et al. | ............... 210/490 |
| 5,433,112 | A | * | 7/1995 | Piche et al. | .................... 73/597 |
| 5,804,727 | A | * | 9/1998 | Lu et al. | ....................... 73/597 |
| 5,882,791 | A | * | 3/1999 | van der Werff et al. | .... 428/364 |
| 6,450,036 | B1 | * | 9/2002 | Ashida et al. | ................. 73/584 |

FOREIGN PATENT DOCUMENTS

DE    34 20 794 A1    12/1984

OTHER PUBLICATIONS

"Ultrasonic measurement and control of polymer melt compositions", Research Disclosure, vol. 263, 1986, p. 127.
Bear et al., "Ultrasonic Pulse Method with Nonlinear Calibration for Quantitative Monitoring of Polymer Blends over a Wide Temperature Range", Analytical Chemistry, American Chemical Society, vol. 65, No. 9, 1993 pp. 1169–1173.

* cited by examiner

Primary Examiner—Hezron Williams
Assistant Examiner—Jacques Saint-Surin
(74) Attorney, Agent, or Firm—Oliff & Berridge, PLC

(57) ABSTRACT

A process for determining the polymer concentration in a spinning dope solution involves measuring the propagation velocity of ultrasonic sound in the solution. The process prevents fluctuations in the polymer concentration as much as possible, and is therefore highly suitable for application in the production of fibers with consistent properties. An ultrasonic device used in the process is easier to clean, install, and calibrate than other presently commercially available devices.

8 Claims, No Drawings

PROCESS FOR DETERMINING THE POLYMER CONCENTRATION IN A SPINNING DOPE SOLUTION

BACKGROUND OF THE INVENTION

1. Field of the Invention

The invention pertains to a process for determining the polymer concentration in a spinning dope solution.

2. Description of Related Art

One area of technology that is a source and motivation for polymer research, particularly with respect to mechanical properties, is the fiber industry. The most widely used fiber-forming processes are melt spinning and solution spinning. In both processes, the polymer is extruded from the orifices of a spinneret. In melt spinning molten polymer is used, while in solution spinning a spinning dope solution is the source of the polymer.

There are many factors that influence the physical and mechanical properties of fibers. If a spinning dope solution is used for the production of fibers, then one of the key parameters that determines these properties is the polymer concentration in the solution. Fluctuations in this concentration should be prevented as much as possible in order to enable the production of fibers with a consistent linear density and consistent properties, such as tensile modulus, relaxation behavior, and fiber strength. Preventing fluctuations in the polymer concentration becomes even more important when a spinning dope solution with a high polymer concentration is used. In this case, a small increase in the concentration could initiate the formation of a non-homogeneous or highly viscous spinning dope solution, which is unsuitable for the production of fibers with consistent properties and often also results in very inconvenient process equipment problems during production of the fibers. Therefore, it is important to determine the concentration as rapidly and accurately as possible.

Several methods are known in the art for determining the polymer concentration in a solution, such as light scattering, density, conductivity, and refractive index measurement, and Infrared, Near Infrared, Raman, and UV spectroscopy. Most commonly, the polymer concentration in a spinning dope solution is determined by measuring the density of the solution. However, said measurement often is not accurate enough to bring fluctuations in the polymer concentration in a spinning dope solution to notice. Furthermore, devices for measuring the density of a spinning dope solution are difficult to clean. These disadvantages become even more important when the measurement is carried out in-line.

SUMMARY OF THE INVENTION

Accordingly, it is the primary object of the present invention to provide a method to determine the polymer concentration in a spinning dope solution rapidly and accurately. Furthermore, the device used for this determination preferably is easier to clean than other presently commercially available devices.

Surprisingly, a process has been found that allows fast and accurate determination of the polymer concentration in a spinning dope solution. The process is characterized in that the determination is carried out by measuring the propagation velocity of ultrasonic sound in the solution.

Fast and accurate determination of the polymer concentration in the spinning dope solution enables prevention of fluctuations in this concentration as much as possible. Therefore, this process is highly suitable for application in the production of fibers with consistent properties. An ultrasonic device used in the process according to the invention is easier to clean, install, and calibrate than other presently commercially available devices. Therefore, the ultrasonic device is also highly suitable for application in the in-line measuring of the propagation velocity of ultrasonic sound in a spinning dope solution in order to determine the polymer concentration in the solution. A method for determining the polymer concentration using ultrasonic sound has been described in R. S. Bear et al., "Ultrasonic pulse method with nonlinear calibration for quantitative monitoring of polymer blends over a wide temperature range," *Analytical Chemistry*, Vol. 65, No. 9, 1169–73 (1993). However, it was not disclosed that this method can be used for determining the polymer concentration in a spinning dope solution. Furthermore, it was not disclosed that this method can be advantageously used for the production of fibers with consistent properties. And even more specifically, it was not disclosed that this method can be used for determining the polymer concentration in a spinning dope solution by the in-line measuring of the propagation velocity of ultrasonic sound in the solution.

DETAILED DESCRIPTION OF PREFERRED EMBODIMENTS

The process according to the invention can be applied using a spinning dope solution that is prepared either batch-wise or continuously by dissolving or dispersing any polymer in any solvent or any solution. Furthermore, a spinning dope solution with any polymer concentration can be used. Therefore, the process can be applied in the production of any fiber. For the production of fibers with a high tensile modulus, where for example one of the aromatic polyamides, or more specifically, poly(p-phenylene terephthalamide), is used as the polymer, it is often required to use a spinning dope solution with a high polymer concentration in order to obtain the desired properties. Since the process is highly suitable for monitoring fluctuations, it can be applied advantageously in the production of said fibers.

A high polymer concentration means a concentration of at least 70%, preferably at least 80% of the concentration at which a non-homogeneous spinning dope solution is formed, or at which the solution becomes too viscous to be used in a spinning process. This high concentration generally is between 10 and 25% by weight. If poly(p-phenylene terephthalamide) is used as the polymer in a sulfuric acid (approx. 99.8% by weight) solution, then this high concentration is about 16 to 21% by weight. When the spin dope concentration is not kept constant such high polymer concentration spinning dope solutions first of all pose problems in the production of fibers with consistent properties, and also lead to very inconvenient problems with the process equipment during production of the fibers.

The determination of a polymer concentration according to the invention can be applied to spinning dope solutions and samples thereof, and can be carried out by measuring the propagation velocity of ultrasonic sound in the solution with an ultrasonic device comprising an emitter and a receiver for ultrasonic sound. The device generates ultrasonic sound waves at the emitter, measures the time it takes before such a wave from the emitter passing through the solution arrives at the receiver, and calculates the propagation velocity as the distance between the emitter and the receiver divided by this time. Ultrasonic sound with a frequency between 50 kHz and 100 MHz can be used. The polymer concentration in a spinning dope solution can be determined by comparing the propagation velocity of ultrasonic sound in this solution with reference propagation velocity values including graphs. These reference values have been measured in spinning dope solutions with known amounts of the polymer, by using the same solvent or solution for dispersing or dissolving the polymer as in the spinning dope solution where the concentration has to be determined.

The propagation velocity (v) of ultrasonic sound in general depends on the density (d) and the adiabatic compressibility (c) of the solution according to the following equation:

$$v = \sqrt{\frac{1}{c*d}}$$

Consequently, if the density of the solution decreases, the propagation velocity of ultrasonic sound in the solution increases. The density is dependent, int. al., on the temperature, the pressure, and the polymer concentration in the solution. Therefore, the propagation velocity of ultrasonic sound in a spinning dope solution is not only dependent on the polymer concentration but also on the temperature and the pressure in this solution. Preferably, the ultrasonic device used for measuring the propagation velocity of ultrasonic sound comprises a temperature sensor in order to enable local adjustment of the temperature in the solution between the emitter and the receiver.

The propagation velocity of ultrasonic sound in a spinning dope solution is also slightly dependent on the flow of the solution in which the measurement takes place. Preferably, the propagation velocity is measured perpendicular to the flow direction. The distance between the emitter and the receiver also plays a role. For an accurate measurement a relatively large distance is preferred, providing the temperature and the pressure of the solution between the emitter and the receiver can be kept constant. A practical distance is between 1 and 10 cm, without it being the intention to limit the invention to this range. Most practical is a distance between 1 and 5 cm.

In order to determine the polymer concentration in a spinning dope solution most accurately by using ultrasonic sound, it is also preferred first of all that the polymer is dissolved or dispersed homogeneously in the solution, secondly that the solution is free from air-bubbles, and finally that the length of any polymer or particle that may be present in the solution is smaller than half the wavelength of the ultrasonic sound used. Furthermore, a relatively large difference in density between the polymer and the solution used to dissolve or disperse this polymer is preferred, in order to attain enough sensitivity for determining the concentration of the polymer most accurately.

If the determination of the polymer concentration in a spinning dope solution is carried out by in-line measuring of the propagation velocity of ultrasonic sound in the solution, then it becomes even more practical to monitor fluctuations in the concentration and to take the appropriate measures to prevent such fluctuations. In-line measuring means that the measurement is carried out continuously or with certain time intervals in a spinning dope solution or in any process stream consisting of this solution. Preferably, the in-line measurement is carried out automatically, for example controlled by an electronic or computer system. Even more preferably, such an electronic or computer system is able to give signals or commands for correcting the polymer concentration in a spinning dope solution as soon as possible when necessary, thereby preventing fluctuations in this concentration as much as possible.

Apart from determining the polymer concentration in a spinning dope solution, an ultrasonic device measuring the propagation velocity of ultrasonic sound in-line often can also be used for the qualitative monitoring of other irregularities in the solution, such as air-bubbles and non-dissolved particles. This monitoring will contribute further to the production of fibers of consistent composition and properties.

The invention will be further illustrated with reference to the following example.

EXAMPLE

Density measurements were carried out in-line using a density meter DIMF 2.0 (Bopp and Reuter), and propagation velocity measurements of ultrasonic sound with a frequency of about 1.5 MHz were carried out using a LIQUISONIC™ (Senso Tech) as ultrasonic device. In-line, in this example, means in a spinning dope solution that flows from a storage tank to a spinneret through a tube with an internal diameter of 16 mm. The emitter and the receiver of the ultrasonic device are arranged in such a way that the generated ultrasonic sound propagates perpendicular to the flow direction, and the distance between the emitter and the receiver is about 2 cm.

Spinning dope solutions containing 18.04, 18.60, 19.03, 19.60 and 19.83% PPTA (poly(p-phenylene terephthalamide)) by weight, respectively, were prepared batch-wise by dispersing the required amount of PPTA in sulfuric acid (99.8% by weight) solutions.

From the results in Table I it can be concluded first that there is an almost linear relation between the density and the PPTA concentration, and second that the sensitivity of a density measurement in this example is about 2.7 kg/m$^3$ per % PPTA. The intrinsic error of such a measurement in this example is about 0.074% PPTA, calculated as the specified reproducibility of the density meter (0.20 kg/m$^3$) divided by the sensitivity of the measurement.

Furthermore, it can also be concluded from the results in Table 1 that the propagation velocity of ultrasonic sound has an almost linear relation with the PPTA concentration, and that the sensitivity of a propagation velocity measurement in this example is about 16.7 m/s per % PPTA. The intrinsic error of said measurement is about 0.0060% PPTA, calculated as the specified reproducibility of the ultrasonic device (0.10 m/s) divided by the sensitivity of the measurement.

This example shows that a propagation velocity measurement of ultrasonic sound is much more sensitive per % PPTA than a density measurement. Furthermore, the intrinsic error in the result of an ultrasonic sound measurement is much lower than the intrinsic error in the result of density measurement. Therefore, it can be concluded that the ultrasonic sound measurements of this example are much more accurate for the determination of the PPTA concentration in the spinning dope solution than the density measurements.

After the measurements the devices were cleaned. It appeared that it was very easy to clean the ultrasonic device, while it was almost impossible to clean the device used for the density measurements.

TABLE I

| PPTA concentration (% by weight) | Density (kg/m³) | Propagation velocity of ultrasonic sound (m/s) |
| --- | --- | --- |
| 18.04 | 1754.80 | 1464.22 |
| 18.60 | 1753.65 | 1474.36 |
| 19.03 | 1752.35 | 1481.40 |
| 19.60 | 1751.22 | 1487.48 |
| 19.83 | 1750.05 | 1494.45 |

What is claimed is:

1. A process of forming fibers having consistent properties from a spinning dope solution having a desired polymer concentration, comprising determining a polymer concentration of a spinning dope solution by measuring a propagation velocity of ultrasonic sound in the spinning dope solution, wherein if the determined polymer concentration differs from the desired polymer concentration for the spinning dope solution, correcting the polymer concentration of the spinning dope solution to correspond to the desired polymer concentration, and extruding the spinning dope solution having the desired polymer concentration through a spinneret to form the fibers.

2. The process according to claim 1 wherein the spinning dope solution comprises a high polymer concentration.

3. The process according to claim 2, wherein the high polymer concentration is from 10 to 25% by weight.

4. The process according to claim 2, wherein the high polymer concentration is from 16 to 21% by weight.

5. The process according to claim 1 wherein a polymer of the spinning dope solution measured is an aromatic polyamide.

6. The process according to claim 5, wherein the aromatic polyamide is poly(p-phenylene terephthalamide).

7. The process according to claim 1 wherein the propagation velocity is measured in-line.

8. The process according claim 1 wherein an ultrasonic device comprising an emitter and a receiver for ultrasonic sound measures the propagation velocity.

* * * * *

UNITED STATES PATENT AND TRADEMARK OFFICE
CERTIFICATE OF CORRECTION

PATENT NO. : 6,672,164 B1
DATED : January 6, 2004
INVENTOR(S) : Willem G. Haanstra et al.

It is certified that error appears in the above-identified patent and that said Letters Patent is hereby corrected as shown below:

Column 4,
Line 21, insert -- in-line -- after "carried out".
Between lines 35 and 36, insert the following paragraph:

-- The density of, and the propagation velocity of ultrasonic sound in, each spinning dope solution were measured in-line at a constant temperature, pressure, and flow velocity of 85ºC, 35 bar, and 20 kg/hour, respectively. --

Signed and Sealed this

Thirtieth Day of March, 2004

JON W. DUDAS
*Acting Director of the United States Patent and Trademark Office*